United States Patent [19]

Adlam et al.

[11] 4,069,314
[45] Jan. 17, 1978

[54] GLYCOPEPTIDE EXTRACT

[76] Inventors: Christopher Adlam, 4A Starts Hill Road, Farnborough, Kent; David Eric Reid, 90 Queensway, West Wickham, Kent, both of England

[21] Appl. No.: 588,313

[22] Filed: June 19, 1975

Related U.S. Application Data

[63] Continuation-in-part of Ser. No. 445,309, Feb. 22, 1974, Pat. No. 4,010,257.

[30] Foreign Application Priority Data

Feb. 23, 1973 United Kingdom ............... 9149/73
Feb. 14, 1974 United Kingdom ............... 6759/74
Aug. 20, 1974 United Kingdom ............. 36522/74

[51] Int. Cl.² .................... A61K 39/02; A61K 35/78
[52] U.S. Cl. .................................... 424/92; 424/195
[58] Field of Search ................................ 424/195, 92

[56] References Cited

PUBLICATIONS

Kwapinski et al. – Chem. Abst. vol. 56, (1962) p. 5272f.
Kwapinski – Chem. Abst., vol. 59 (1963) p. 10485b.
Merchant et al. – Veterinary Bacteriology & Virology – 6th Edit. (1961) p. 258.

*Primary Examiner*—Sam Rosen
*Attorney, Agent, or Firm*—Donald Brown

[57] ABSTRACT

Immunostimulating glycopeptides obtainable from the cell walls of immunostimulating bacteria belonging to the Mycobacteriaceae or Actinomycetaceae Family and methods of isolating the glycopeptides.

11 Claims, No Drawings

GLYCOPEPTIDE EXTRACT

This application is a continuation-in-part of U.S. patent application Ser. No. 445,309 filed Feb. 22, 1974, now U.S. Pat. No. 4,010,257.

The present invention relates to glycopeptides having pharmacological activity, the extraction of the glycopeptides from bacterial cells and their adaptation for medicinal use.

It has previously been known that certain bacteria belonging to the Actinomycetaceae or Mycobacteriaceae Families of Prevot's classification (1), have immunostimulating properties.

As used herein 'immunostimulating' means capable of stimulating a non-specific immune response in mammals, and birds that is, capable of conferring on mammals and birds a resistance to tumours and various pathogens, such as viruses, bacteria (12), and parasites (13), in the absence of antigenic affinity between the pathogen and the products of immunostimulation; as well as behaving as an adjuvant in mammals and birds.

It has now been found that glycopeptides having immunostimulating properties may be obtained from the abovementioned bacteria.

The present invention provides an immunostimulating glycopeptide suitable for use in conferring on mammals or birds a resistance to tumours and various pathogens which glycopeptide is obtainable from the cell wall of an immunostimulating bacterium belonging to the Actinomycetaceae or Mycobacteriaceae families of Prevot's classification, which glycopeptide is substantially insoluble in water, physiological saline, methanol, ethanol, phenol, chloroform, dioxan, pyridine, dimethylformamide, diethylene glycol, and hexane; has an absorption in the Infra-red spectrum at 1550 and 1660 cm$^{-1}$ consistent with the presence of peptide; has an absorption in the Infra-red spectrum between 950 and 1100 cm$^{-1}$ with a maximum absorption at 1050 to 1070 cm$^{-1}$ consistent with the presence of carbohydrate; has little or no lipid absorption in the Infra-red spectrum at 2850 to 2950 cm$^{-1}$; and which glycopeptide, after intravenous administration, increases the liver and spleen weight of mice and increases the life expectancy of mice with tumours.

Genera belonging to one or other of the Actinomycetaceae or Mycobacteriaceae families tht may be mentioned are Actinomyces, Nocardia, Streptomyces, Micromonospora, Corynebacterium (also known as Propionibacterium) both aerobic and anaerobic species, Actinobacterium (also known as Bifidobacterium), Erysipelothrix, Listeria and Mycobacterium.

Species belonging to the Genus Corynebacterium which may be mentioned include *C. anaerobium, C. granulosum, C. liquefaciens, C. pyogenes, C. lymphophilum, C. hepatodystrophicans, C. adamsoni, C. parvum, C. avidum, C. diphtheroides, C. renale cuniculi, C. acnes, C. equi,* and *C. ovis.*

There is considerable controversy concerning the taxonomy of the Corynebacteria. Nevertheless any references to the species *C. parvum* herein are intended to include the strain having Wellcome Culture Collection number CN 6134 which strain was obtained from the Pasteur Institute and has the Pasteur Institute's Culture number 4685, and has previously been described as *C. anaerobium* (see for example, Ref. 9).

The composition of the glycopeptides of the present invention is subject to variation due to such factors as genetic variation depending on the particular strain used as a source of bacterial cells and the particular methods used in the culture of those cells. Variation may also occur arising out of the degree of purity achieved by the isolation process used, for example, due to incomplete removal of external protein attached to the glycopeptides.

Desirably glycopeptides of the present invention comprise from 30 to 45%, preferably about 40%, by weight of carbohydrate.

Preferably the glycopeptides comprise according to microanalysis, from 38 to 43% Carbon, from 7 to 10% Nitrogen and from 5 to 7% of Hydrogen, the percentages being by weight of the dry glycopeptide.

The glycopeptides of the present invention may be extracted from the bacterial cells by preparing a culture of the bacterial cells; recovering cultured bacterial cells from the culture; optionally lysing the cultured bacterial cells to produce a lysate thereof; and subjecting the cultured bacterial cells or lysate thereof to biphasic solvent extraction so as to yield the glycopeptide as insoluble residue.

The bacterial cells from which the glycopeptides of the present invention are obtained, may be obtained from any known source. In general the bacterial cells may be initially obtained from mammals or birds infected with the required bacterium, for example, *C. parvum* may be obtained from the blood of patients suffering from a septicaemia whilst *C. renale cuniculi* is often associated with normal mammalian kidneys. Some bacteria, however can be obtained from more than one habitat, for example, *C. parvum* may also be obtained from the skin of some normal humans.

Bacterial cells which have immunostimulating properties (from which the glycopeptides of the present invention are obtainable) may be readily identified by their ability to increase spleen and liver weight in mice and/or their adjuvant activity in mice (9) and their ability to produce resistance to tumours in mice (14).

Any culture of the bacterial cells prepared by methods already known, may be used as a material for the extraction of the glycopeptide. Advantageously freshly isolated strains are stored in a freeze-dried condition before being cultured in a nutrient medium, such as Robertson's cooked meat medium (3) supplemented with 1% w/v glucose and 5% v/v horse serum. The culture is desirably maintained at a temperature above ambient, for example, about 37° C for several days, conveniently 5 to 7 days and preferably without disturbance of the culture medium. In order to increase the yield of culture, the products of the initial culture may be used to seed further quantities of growth medium, for example, a medium containing 1% w/v glucose, wherein growth takes place under similar conditions. Other suitable growth media include Todd-Hewitt broth (4) and Thioglycollate broth (5). In order that the maximum yield of cells is obtained in the minimum time, successive subculture of the cells is required and each subculture is preferably effected in the logarithmic phase of growth and on each occasion the inoculum is preferably about 10% by volume of the succeeding culture though for the last stage the inoculum is conveniently 2% to 3% by volume of the succeeding culture.

The cultured bacterial cells may be recovered from the culture medium by any conventional process for harvesting such media, for example, by centrifugation. Desirably the cultured bacterial cells are then repeatedly washed, for example with aqueous 0.85% w/v sodium chloride or with distilled water, prior to extraction.

Lysis of the cultured bacterial cells may be effected by any conventional technique for the lysis of cells, for example, by the use of physico-chemically acting agents such as hypertonic buffers with mechanical agitation of the viscous lysate; or mechanical lysis, for example by use of ultrasonic sound waves; by intracellular cavitation; by passage at low temperature and high pressure through a narrow orifice as in a press such as the Hughes press (6); or by mechanical agitation in a homogeniser or grinder (7). Desirably the broken cell walls are separated from the other constituents of the lysate, for example, by centrifugation. Centrifugation may be effected at 15,000 to 25,000, for example, 20,000g for about 30 to 90 minutes, for example, 1 hour. Conveniently a preliminary centrifugation is carried out at a low speed, for example at about 300g. for 3 minutes, the supernatant from this stage then being used for the main centrifugation stage at higher speed, intact cells remaining in the sediment.

Biphasic solvent extraction of the broken cell walls, and/or cultured whole bacterial cells, and/or the lysate thereof so as to yield the glycopeptide is effected with aqueous aryl alcohol and the glycopeptide isolated from the cell constituents not extracted in the aqueous phase. As used herein 'aryl alcohol' means a compound wherein a hydroxy nucleus is directly attached to an aromatic nucleus, for example, an optionally substituted phenol such as a cresol, but most preferably unsubstituted phenol.(see Example, Ref.16)

The biphasic solvent extraction is effected by contacting with water and the aryl alcohol for a period of time at a temperature of from 0° C to 100° C, preferably from 15° to 70° C, conveniently with stirring. A suitable period of time is from a few minutes to a few hours depending on the temperature employed. In the case where phenol is used, a particularly suitable temperature is 68° C at which stirring may be carried out for 15 minutes.

The concentration of aryl alcohol in the aryl alcohol-water mixture may be varied somewhat, it being necessary to bear in mind that one must ultimately obtain a 2-phase system, each phase being fully saturated with the other. In the case of phenol, the phenol concentration in the phenol-water mixture may be from 10 to 90% v/v, but most preferably from 40 to 55% v/v.

The mixture is then centrifuged at about 5,000 to 10,000g for 45 to 15 minutes, for example, at 8,000g for 30 minutes, to yield four layers: a solid pellet containing cell debris, above which are in turn the alcoholic phase, a white interphase region, and the aqueous phase. In the case of a process not involving lysis, little or no material is present in the interphase region, centrifugation yeilding only three layers: a solid pellet containing unbroken cells, above which are in turn the alcoholic phase, and the aqueous phase.

The aqueous phase and alcoholic phases are discarded and desirably the biphasic solvent extraction is repeated on the remaining material preferably until the aqueous and alcoholic phases, after centrifugation, are colourless (or in the case of a coloured alcohol, are unchanged in colour in the course of extraction). Alternatively only the aqueous phase is discarded, the remaining material including the alcoholic phase, being reextracted if desired.

The material remaining after the aqueous phase (and if desired, the alcoholic phase) has been discarded is then desirably dialysed against water to remove the aryl alcohol (or residual aryl alcohol, respectively). Dialysis is effected for several days, desirably at a temperatue below ambient, for example, at about 4° C.

After dialysis a sediment is obtained comprising the following layers: a dark coloured lower layer (not present when the alcoholic phase has been discarded after centrifugation), a brown cream coloured layer having an oily consistency and an upper layer comprising a white finely divided suspension which may then be collected to yield the immunostimulating glycopeptides of the present invention which are desirably washed with distilled water or physiological saline (0.85% w/v aqueous sodium chloride).

The glycopeptides of the present invention may be used therapeutically or prophylactically in conferring on mammals and birds a resistance to tumours and various pathogens, inhibiting the growth of such tumours and pathogens and/or decreasing their extent, by administration of an effective therapeutic or prophylactic dosage of the glycopeptides. Tumours that may be mentioned in this context include leukaemias, Hodgkin's disease, carcinoma of the lung, bladder and breast, melanoma and Burkitt's lymphoma. Bacterial pathogens that may be mentioned include *Bordetella pertussis* and *Brucella abortus. Parasitic pathogens include protozoal pathogens such as malaria.*

The magnitude of the therapeutic or prophylactic dosage of glycopeptide will of course vary with the nature and severity of the tumour of the pathogenic infection concerned, with the particular glycopeptide and its route of administration. In general the dosage range lies from 0.0001 to 20, preferably 0.1 or 0.5 to 10, and most preferably from 0.7 to 2mg of glycopeptide per kg. bodyweight of the mammal or bird to which the glycopeptide is to be administered.

Any conventional mode of administration may be used at the discretion of the attending physician and depending on the nature and location of the tumour or pathogenic infection concerned. Thus administration may be by the oral or pulmonary route though usually administration is by injection subcutaneously, intramuscularly, intraperitoneally or, preferably, intravenously. If desired "injection" may comprise infusion over an extended period of time, for example, over several hours.

The glycopeptides may be formulated into a pharmaceutical composition for use in a method of treatment or prophylaxis as described hereinbefore, by any conventional pharmaceutical technique involving inter alia the step of admixture of the glycopeptides with one or more pharmaceutically acceptable carriers. The nature of the composition will of course depend on the route chosen for administration. Thus for oral administration, a composition of a glycopeptide of the present invention may be presented as a discrete unit such as a capsule, cachet or tablet each containing a predetermined amount of the glycopeptide; as a powder or granules; or as a suspension in an aqueous liquid, a non-aqueous liquid an oil-in-water emulsion or a water-in-oil emulsion. For pulmonary administration, a composition of a glycopeptide of the present invention may be present as an inhalation composition.

A pharmaceutical composition of the present invention intended for administration by injection comprises a glycopeptide of the present invention suspended in an inert pharmaceutically acceptable liquid diluent. The compositions for injection must of course be sterile and isotonic with the blood of the mammal or bird into which they are to be administered. A suitable diluent is water and a suitable injection composition for use in humans is a suspension of the glycopetide in physiological siline (0.85% w/v aqueous sodium chloride). Advantageously the glycopeptide is suspended in a sterile diluent under aseptic conditions. Sterilisation of the injection compositions may be effected by conventional techniques, for example, by the addition of formalin to a concentration of about 0.5% v/v. Desirably a preservative, for example, thiomersalate conveniently at a concentration of 0.01% w/v is included in the injection compositions.

The injection compositions of the present invention may be rendered isotonic by any conventional technique, for example, by dialysis against a salt solution that is isotonic with the blood of the mammal or bird to be injected. Any salt solution suitable for use as an injection medium, for example, physiological saline (0.85% w/v aqueous sodium chloride) or isotonic phosphate buffer may be used.

The injection compositions may be prepared either as a concentrated injection composition for dilution prior to use or as an injection composition ready for use. In the latter case the concentration of the immunostimulating glycopeptide is desirably from 20 to 2mg/ml; preferably of the order of 7mg/ml. Conveniently the injection compositions may be freeze-dried, for example, from 5% w/v aqueous sucrose, for reconstitution with water just before use.

A further use of glycopeptides of the present invention is as an adjuvant; or as an ingredient in a vaccine having another active ingredient. An example of such a use, is the substitution of the glycopeptide for the heat killed bacterial element of Freund's complete Adjuvant (a water-in-oil emulsion of an active ingredient in a mineral oil also containing heat killed bacteria), and an example of a vaccine containing the glycopeptide as an adjuvant is a vaccine for immunisation against Brucella.

In order that the present invention may be more fully understood, the following examples are given, purely by way of illustration and are not to be construed as limiting the scope of the present invention.

EXAMPLE 1

Isolation of Immunostimulating glycopeptide of *C. parvum* cells

A. Preparation of cultured *C. parvum* cells

Freeze dried cells of *C. parvum* (0.2 to 0.5mg) (Wellcome Culture No. CN 6134) were seeded into a screwed cap bottle containing Robertson's cooked meat medium (20ml) (3) supplemented with glucose (1% w/v) and horse serum (5% v/v). After static incubation of 37+ C for 6 days, incubation was continued for 6 days in 2 liter capacity bottles (1800ml of broth) and then for about 7 days in 15 liter capacity bottles. In each case the volume of seed mixture used about 10% by volume of the broth to be seeded, except for the last stage when a 2½% inoculum was used.

The cultured cells were then harvested by subjecting the final culture mixture to centrifugation at 2000g, for 2 hrs. The supernatant was discarded and the cells washed repeatedly by resuspending the sedimented cells in physiological saline and centrifuging the suspension as before.

B. Cell lysis

The washed cells (10g wet weight) were mixed with Ballotini glass beads (35g of No.14) and a small quantity of physiological saline about 1ml).

The mixture was then subjected to mechanical agitation in a Novotny disintegrator (8) for 15 minutes with the paddle rotating at 2000 r.p.m. The resulting slurry was then diluted with a further quantity of physiological saline (ca. 10ml) and filtered in a coarse sintered glass separator to remove the glass Ballotini. The residue was resuspended in physiological saline (ca. 10ml) and centrifuged at 20,000g for 1 hour to sediment out the broken cell walls.

C. Extraction of *C. parvum* cell walls

To the *C. parvum* broken cell walls (20g wet weight) were added distilled water (350ml) and aqueous phenol (0% w/v, 350ml), both at 68° C. The mixture was incubated at 68° C for 15 minutes constant stirring, cooled in an ice bath and the mixture then centrifuged at 8000 g for 30 mins at 4° C, Four distinct layers were observed in the centrifuge vessel, a pellet, a lower phenolic phase, a white interphase layer, and an upper aqueous phase. The aqueous phase was discarded and the remaining layers resuspended in a further quantity of distilled water (350ml) at 68° C and re-extracted as before. Again the upper aqueous phase was discarded and the remaining layers were then combined and dialysed against running tap water for 4 days followed by distilled water at 4° C for a further 3 days in order to remove the phenol.

After 1 week a sediment of three layers was present in the dialysis tubing. A lower dark coloured layer comprised broken cells bound up with DNA. A second browncream coloured layer had an oily constistency (both of these layers had little or no immunostimulating activity). The upper white layer was collected, after water had been removed from the dialysis tubing, to give the glycopeptide, (hereinafter referred to as glycopeptide A) of which the properties are described herein below.

Physical Properties

The glycopeptide possessed the following properties:

a. It was slightly soluble in dimethyl sulphoxide. It was insoluble in water, phenol, ethanol, methanol, chloroform, dioxan, pyridine, dimethylformamide, diethylene glycol, hexane, acetone, ether and physiological saline;

b. It was substantially lipid-free (J. Falch et al J. Biol. Chem. 226 497 (1957));

c. When suspended in a phenol-water mixture, it became concentrated in the interphase region;

d. It had a chemical composition as determined by microanalysis, the amounts representing percentages by weight: Carbon 39.03; Hydrogen 6.24; Nitrogen 9.03; Phosphorus Trace; Ash 5.4; Silica 1.48; Sulphur below 0.2; and Oxygen, by difference, of the order of 40. Carbon, Hydrogen, and Nitrogen were determined in a Perkin-Elmer 240 semi-automatic analyser.

e. It had an Infra-red analysis of the solid material (1.5mg) dispersed in a standing 16mm diameter potassium chloride disc, having the following absorbances per mg. of solid glycopeptide:

| bond | Wavelength cm$^{-1}$ | absorbance/mg |
|------|----------------------|---------------|
| CO-NH | 1660 | 0.78 |
| C-OH | 1050–1070 | 0.29 * |

-continued

| bond | Wavelength cm⁻¹ | absorbance/mg |
|---|---|---|
| C-H | 2850-2950 | 0.004 * |

*relative to albumin

Details of the actual infra-red spectrum obtained are given hereinbelow.

f. Chromatographic fractionation of a hydrolysate of the glycopeptide indicated the presence of certain aminoacids and sugars as follows:

amino acids ornithine, alanine, valine, leucine and aspartic acid; the hydrolysis being effected in 6N HCL in sealed ampoules for 18 hours at 100° C, the residue being dissolved in water and Chromatography being effected on Whatman 3 mm paper using ascending chromatography for 18 to 24 hours with a solvent comprising butanol (60ml), acetic acid (15ml), and water (25ml) followed by development with a ninhydrin spray, for amino acids; and sugars galactose, glucose, mannose and trace amounts of arabinose; the hydrolysis being effected in 2N HCl in sealed ampoules for 3 hours at 100° C, the residue being dissolved in pyridine and chromatography being effected on Whatman 3 mm paper using descending chromatography for 18 to 24 hours with a solvent comprising butanol (60ml), pyridine (40ml), and water (30ml) followed by development with an Aniline-Oxalate spray for sugars (P. Novotny, J. Med. Microbiol. 2 81 (1969));

g. A Biuret test for protein was carried out (Ref. 10) on the glycopeptide which took up a blue colouration which was not washed off.

h. The glycopeptide yielded a positive response to the Anthrone test (Ref. 11), the reaction solution turning blue-green.

EXAMPLE 2 and 3

Isolation of immunostimulating glycopeptide of *C. parvum* cells.

Two further glycopeptide preparations (hereinafter referred to as glycopeptides B and C) were obtained by the process described in Example 1, using the same *C. parvum* strain.

EXAMPLE 4

Isolation of immunostimulating glycopeptide of *C. parvum* Cells

A further glycopeptide preparation (hereinafter referred to as glycopeptide D) was obtained from the *C. parvum* strain used in Example 1 by the process described in Example 1 but with the following difference: the mixture of lysate, water and phenol was centrifuged at 1,500g for 1 hour (instead of at 8,000g for 30 minutes).

EXAMPLE 5

Properties of glycopeptides of Examples 1 and 2

1. Infra-red analyses of glycopeptides A and B dispersed in standard 16mm diameter potassium halide discs yielded the following results:

| wave-length cm⁻¹ | | Glycopeptide A (1.57mg in KCl disc) | | | Glycopeptide B (1.50mg. in KBr disc) | | |
|---|---|---|---|---|---|---|---|
| | | A | %Abs | A° | A | %Abs | A° |
| 850 | min | .12 | 22 | | .02 | 5 | |
| *1055 | max | .68 | 79 | .58 | .31 | 50 | .66 |
| 1152 | infl. | .37 | 58 | | .19 | 36 | |
| 1200 | min | .20 | 36 | | .10 | 20 | |
| 1380 | doublet | | | | | | |
| 1405 | max | .49 | 67 | .42 | .26 | 45 | .55 |
| 1480 | min | .26 | 45 | | .15 | 29 | |
| 1545 | max | .72 | 81 | .62 | .35 | 55 | .74 |
| 1575 | min | .64 | 77 | | .32 | 52 | |
| 1605 | infl. | .78 | 83 | | — | — | |
| 1660 | max | 1.17 | 93 | 1.00 | .47 | 66 | 1.00 |
| 1900 | base | .03 | 5 | | .07 | 14 | |
| 2920 | max | .37 | 57 | .32 | .24 | 42 | .51 |
| 3400 | max | 1.10 | 92 | .94 | .50 | 70 | 1.06 |

*Max. almost flat, 1045–1070 cm⁻¹
min = minimum
max = maximum
infl = inflection
A = absorbance
%Abs = percentage absorption
A° = absorbance relative to peptide band at 1660 cm⁻¹

2. Microanalysis of glycopeptide B (under the same conditions as in Example 1. (d)) yielded the following composition: Carbon 39.77%, Hydrogen 6.40%, Nitrogen 8.15%, Ash 2.8%, Silica 0.84% and less than 0.2% of each of Phosphorus and Sulphur, the percentage values given being by weight of the dry weight of the glycopeptide.

EXAMPLE 6

Pharmaceutical composition suitable for injection.

The glycopeptide of Example 1 (70mg) was suspended in a solution of physiological saline (0.85% w/v aqueous sodium chloride, 10ml) containing 0.01% w/v thiomersalate. The suspension was sterilised by the addition of 0.1% w/v formalin for 24 hours whereupon the formalin was removed by centrifugation at 38,000g for 30 minutes. After washing twice in physiological saline the glycopeptide was then resuspended in physiological saline (10ml) containing 0.01% w/v thiomersalate and distributed into 1ml glass ampoules which were then sealed.

EXAMPLE 7

Properties of glycopeptides of Examples 2 & 3

1. Infra-red analyses of glycopeptides B and C dispersed in standard 16mm diameter potassium chloride discs yielded the following results.

| wave-length cm⁻¹ | | Glycopeptide C (1.45 mg) | | | wave-length cm⁻¹ | | Glycopeptide D (1.54mg) | | |
|---|---|---|---|---|---|---|---|---|---|
| | | A | %Abs | A° | | | A | %Abs | A° |
| 925 | | .16 | 31 | | 860 | min | .145 | 28 | |
| 1063 | max | .55 | 72 | .44 | 1061 | max | .66 | 78 | .66 |
| 1155 | max | .33 | 53 | | 1152 | infl | .36 | 56.5 | |
| 1202 | min | .195 | 36 | | 1200 | min | .19 | 35 | |
| 1382 | doublet | .425 | 62.5 | .34 | 1382 | doub | 48 | 67 | .48 |
| 1412 | Max | .47 | 66 | | 1410 | max | .47 | 66 | |

-continued

| wave-length cm$^{-1}$ | Glycopeptide C (1.45 mg) | | | wave-length cm$^{-1}$ | Glycopeptide D (1.54mg) | | |
| --- | --- | --- | --- | --- | --- | --- | --- |
| | A | %Abs | A° | | A | %Abs | A° |
| 1482 min | .26 | 45 | | 1480 min | .25 | 44 | |
| 1557 max | .86 | 86 | .69 | 1570 max | .74 | 82 | .74 |
| 1605 min | .74 | 82 | | | | | |
| 1900 | .035 | 8 | .33 | 1900 base | .035 | 8 | |
| 2940 max | .41 | 61 | | 2940 maX | .38 | 58 | .38 |
| 3400 max | 1.25 | 94 | 1.00 | 3400 max | .96 | 89 | .96 |
| 1660 max | 1.25 | 94 | 1.00 | 1650 max | 1.00 | 90 | 1.00 | min = minimum
max = maximum
infl = inflection
A = absorbance
%Abs = percentage absorption
A° = absorbance relative to peptide band at 1660 cm$^{-1}$ 2. Microanalysis of glycopeptide C (as in Example 1 (d)) yielded the following composition: Carbon 38.51%, Hydrogen 5.81%, Nitrogen 8.22%, Phosphorus 0.23%, Sulphur >0.3%, Ash 4.2% and Silica 1.81%, the percentage values given being by weight of dry weight of the extract.

EXAMPLE 8

Biological properties of glycopeptide of *C.parvum* cells

1. Lympho — recticular stimulating activity

10 Olac mice (Random-bred, W-Swiss females from 16 to 20g bodyweight) each received a single intravenous injection containing the glycopeptide of Example 3 (1.4mg) in 0.85% w/v aqueous sodium chloride (0.2ml). After 10 days the mice were sacrificed and their spleens and livers recovered and weighed. 10 similar control mice each received a single intravenous injection of aqueous sodium chloride (0.85% w/v) and after 10 days were sacrificed, and their spleens and livers recovered and weighed. The results are shown in Table 1 as the means organ weight in mg. corrected for a 20g mouse body weight.

Table 1

| Effect of glycopeptide in increasing spleen and liver weights in mice | | |
| --- | --- | --- |
| | Spleen Weight (mg) | Liver Weight (mg) |
| Controls | 102 | 1060 |
| Test Mice | 250 | 1741 |

2. Anti-tumour activity

20 Olac mice (females each of 16–20g bodyweight) were each injected intraperitoneally with an allogeneic mouse sarcoma 180T/G (10$^5$ cells) (Ref.16). 24 hrs later 10 test mice each received a single intravenous injection containing the glycopeptide of Example 3 (1.4mg) in aqueous sodium chloride (0.85% w/v). The remaining 10 control mice each received a single intravenous injection of aqueous sodium chloride (0.85% w/v).

Table 2

| The effect of glycopeptide extracted from C. parvum on Tumour 180/TG in mice | | |
| --- | --- | --- |
| Days from glycopeptide injection date | Number of mice surviving | |
| | Controls | Test Mice |
| 15 | 10 | 10 |
| 16 | 10 | 9 |
| 17 | 9 | 9 |
| 18 | 6 | 9 |
| 19 | 4 | 9 |
| 20 | 4 | 8 |
| 21 | 3 | 7 |
| 22 | 2 | 7 |
| 23 | 2 | 7 |
| 24 | 2 | 7 |
| 25 | 2 | 5 |
| 26 | 1 | 5 |
| 27 | 1 | 5 |
| 28 | 1 | 5 |
| 29 | 1 | 5 |
| 30 | 1 | 5 |

Mouse fatalities were then recorded over a period of 30 days.

RESULTS

Table 2 shows the effect of the glycopeptide in improving life expectancy of mice injected intraperitoneally with the mouse sarcoma.

EXAMPLE 9

Isolation of Immunostimulating glycopeptide from *C.parvum* cells

A further glycopeptide preparation (hereinafter referred to as glycopeptide E) was isolated from lysed cells prepared as in Example 1. The isolation procedure of Example 1 was then followed except that the phenolic phase was discarded at the same time as the aqueous phase. Dialysis was effected as before in order to remove residual phenol and yielded a sediment of only two layers: a lower dark coloured layer and an upper white layer. The latter was collected as before to yield the glycopeptide E.

EXAMPLE 10

Isolation of immunostimulating glycopeptide from *C.parvum* cells

A further glycopeptide preparation (hereinafter referred to as glycopeptide F) was obtained using the *C.parvum* strain and the process described in Example 1.

EXAMPLE 11

Biological properties of glycopeptides of Example 9 and 10.

The lymphoreticular stimulating activity of glycopeptides E and F was studied using the procedure given in Example 8.1, yielding the following results:

| | spleen weight (mg) | liver weight (mg) |
| --- | --- | --- |
| Controls (5) | 88 | 1155 |

-continued

|  | spleen weight (mg) | liver weight (mg) |
|---|---|---|
| Mice receiving 1.0mg of glycopeptide E (5) | 227 | 1724 |
| Controls (5) | 91 | 1098 |
| Mice receiving 1.4mg of glycopeptide F (10) | 185 | 1481 |

The spleen and liver weights given are the mean values. The numbers in brackets are the numbers of mice involved in the tests.

EXAMPLE 12

Extraction of whole C. parvum cells

C. parvum whole cells were freeze dried and to 20 g dry weight was added distilled water (400 ml) and aqueous phenol (90% w/v, 400 ml) both at 68° C. The mixture was incubated at 68° C for 15 minutes with constant stirring, cooled in an ice bath and the mixture then centrifuged at 8000 g for 30 minutes at 4° C. Four distinct layers were observed in the centrifuge vessel, a pellet, a lower phenolic phase, a very small amount of a white interphase layer, and an upper aqueous phase. The aqueous and phenolic phases were discarded and the pellet and interphase material resuspended in a further quantity of distilled water (400 ml) at 68° C together with phenol (400 ml) also at 68° C and re-extracted as before.

Extractions were repeated using fresh water and phenol until the phenol layer was colourless. It was noticeable that the interphase material increased in amount with each extraction process.

The final aqueous and phenolic phases were discarded and the pellet and interphase materials combined and dialysed against running tap water for 4 days followed by distilled water at 4° C for a further 3 days in order to remove the phenol.

After dialysis a sediment of 2 layers was present in the dialysis tubing. A lower grey/green oily layer possessing little or no immunostimulating activity and an upper white layer which possessed the activity of the present invention.

The upper white layer was collected, after water had been removed from the dialysis tubing, to give the glycopeptide. The C. parvum strain was the same as in Example 1, namely Wellcome Culture No. C.N. 6134, which was obtained from Pasteur Institute Culture No. 4685.

Physical Properties

The glycopeptide possessed the following properties:
a. It was slightly soluble in dimethyl sulphoxide. It was insoluble in water, phenol, ethanol, methanol, chloroform, dioxan, pyridine, dimethylformamide, diethylene glycol, hexane, acetone, ether and physiological saline;

b. It was substantially lipid-free (J. Falch et al J. Biol. Chem. 226 497 (1957));

c. It had a chemical composition as determined by microanalysis, the amounts representing percentages by weight: Carbon 41.3; Hydrogen 6.4; Nitrogen 10.85; Phosphorus 0; Silica 0; Sulphur below 0.2; and Oxygen, by difference, of the order of 40. Carbon, Hydrogen, and Nitrogen were determined in a Perkin-Elmer 240 semi-automatic analyser.

d. It had an Infra-red analysis of the solid material dispersed in a standard 16 mm diameter potassium chloride disc, having absorbances at 1055 $cm^{-1}$ and 1545 and 1660 $cm^{-1}$ respectively, and an absorbance at 2920 $cm^{-1}$ consistent with the pressure of little or no lipid.

e. Chromatographic fractionation of a hydrolysate of the glycopeptide indicated the presence of certain sugars as follows:

Sugars galactose, glucose, mannose and trace amounts of arabinose;

the hydrolysis being effected in 2N HCl in sealed ampoules for 3 hours at 100° C, the residue being dissolved in pyridine and chromatography being effected on Whatman 3 mm paper using descending chromatography for 18 to 24 hours with a solvent comprising butanol (60 ml), pyridine (40 ml), and water (30 ml) followed by development with an Aniline-Oxalate spray for sugars (P. Novotny, J. Med. Microbiol. 2 81 (1969));

f. A Biuret test for protein was carried out (Ref. 10) on the glycopeptide which took up a blue colouration which was not washed off.

g. The glycopeptide yielded a positive response to the Anthrone test (Ref. 11), the reaction solution turning blue-green.

EXAMPLE 13

Biological Properties of glycopeptide of Example 12

A. The lymphoreticular stimulating activity of the glycopeptide was studied using the procedure given in Example 8.1, yielding the following results:

|  | Spleen weight mg | Liver weight mg |
|---|---|---|
| Controls | 88 | 1155 |
| Test mice | 526 | 2624 |

The spleen and liver weights given are the mean values.

B. The anti-tumour activity of the glycopeptide was studied.

A test group comprising 10 Olac mice (females each of 16–20 g bodyweight) were each injected intravenously with glycopeptide (0.43 mg) in aqueous sodium chloride (0.85% w/v).

After 7 days both groups of mice were challenged by intraperitoneal injection of an allogeneic mouse sarcoma 180T/G ($10^{15}$ cells) Ref. 16. Mouse fatalities were then recorded over a period of 30 days.

RESULTS

Table 3 shows the effect of the glycopeptide in improving life expectancy of mice challenged with the mouse sarcoma.

Table 3

The effect of glycopeptide extracted from C. parvum on Tumour 180T/G in mice

| Days from Challenge | Number of mice surviving | |
|---|---|---|
|  | Controls | Test mice |
| 16 | 9 | 10 |
| 17 | 8 | 10 |
| 18 | 7 | 10 |
| 19 | 7 | 10 |
| 20 | 7 | 10 |
| 21 | 5 | 10 |
| 22 | 2 | 6 |
| 23 | 1 | 4 |
| 24 | 1 | 3 |
| 25 | 1 | 3 |
| 26 | 1 | 2 |

Table 3-continued

| The effect of glycopeptide extracted from C. parvum on Tumour 180T/G in mice | | |
|---|---|---|
| Days from | Number of mice surviving | |
| Challenge | Controls | Test mice |
| 27 | 1 | 1 |
| 28 | 1 | 1 |
| 29 | 1 | 1 |
| 30 | 1 | 1 |
| Harmonic mean Survival time (in days) | 21.95 | 25.6 |

C. Effect of glycopeptide on histamine sensitisation in mice (Ref. 17).

Groups of 10 NIH mice (adult females each of 16–20 g bodyweight) were injected with aqueous sodium chloride (0.85% w/v) containing 0; 0.43 or 1.4 mg of glycopeptide. After 7 days all groups were challenged with histamine phosphate and deaths recorded over 24 hours (Ref. 17).

Results

Table 4 shows the effect of the glycopeptide in sensitising the mice to histamine.

Table 4

| The effect of glycopeptide extracted from C. parvum in sensitising mice to histamine | | |
|---|---|---|
| Dose of glycopeptide (mg per mouse) | Dose of histamine base (mg/mouse) | number of mice surviving (after 24 hours) |
| 1.4 | 0.25 | 0 |
|  | 0.125 | 2 |
|  | 0.0625 | 7 |
| 0.43 | 0.5 | 1 |
|  | 0.25 | 4 |
|  | 0.125 | 6 |
| 0 (controls) | 10 | 10 |
|  | 5 | 10 |
|  | 1 | 9 |
|  | 0.5 | 10 |

D. Toxicity Data for the Glycopeptide

The following tests of the U.S. Dept. of Health, Education and Welfare Public Service, Regulations for the Manufacture of Biological Products Title 42 Part 73, Division of Biologies standards, N.I.H. Bethesda, Md., U.S.A. were carried out on the glycopeptide.

1. Mouse Weight Loss

Groups of 10 male mice (14–16 g) received intraperitoneal injections (0.2 ml volume) of varying dilutions of the whole cells of C. parvum (starting material for obtaining the glycopeptide); the glycopeptide obtained by the phenol and water extraction; and saline. The mice were weighed daily for 7 days and the weight loss compounded as a percentage of the starting weight.

RESULTS

The mean mouse weights during the test period are given in Table 1 from which it may be seen that:
  a. no fatalities were recorded during the test period;
  b. that in all cases the starting weights were recovered within the required 3 days and in fact the starting weights were recovered within 2 days of the injection of the test material, in all cases; and
  c. no significant differences in the recovery of lost weight were found between the groups injected with the known whole cell C. parvum material and the groups injected with the new glycopeptide of the present invention.

Table 1.

| | Material injected | Dosage mg per mouse | Days after injection | | | | | | | |
|---|---|---|---|---|---|---|---|---|---|---|
| | | | 0 | 1 | 2 | 3 | 4 | 5 | 6 | 7 |
| | Saline | — | 100 | 106 | 111 | 121 | 126 | 130 | 134 | 139 |
| A. | C. parvum | 1.4 | 100 | 91 | 101 | 115 | 123 | 128 | 135 | 148 |
| | | 0.47 | 100 | 99 | 107 | 119 | 124 | 126 | 131 | 134 |
| | whole cells | 0.16 | 100 | 103 | 106 | 119 | 125 | 129 | 135 | 139 |
| | Saline | — | 100 | 106 | 116 | 126 | 135 | 141 | 149 | 156 |
| B. | Glycopeptide | 1.4 | 100 | 90 | 106 | 111 | 125 | 131 | 137 | 142 |
| | | 0.47 | 100 | 96 | 108 | 116 | 127 | 134 | 138 | 147 |
| | | 0.16 | 100 | 101 | 111 | 119 | 127 | 131 | 136 | 143 |

2. Pyrogenicity

Groups of 2 rabbits received intravenous injections (0.4 ml volume) of varying dilutions of whole cells of C.parvum (known material also used as starting material for obtaining glycopeptide); the glycopeptide obtained by the phenol and water extraction; and saline. Rectal temperature rise was recorded by thermocouple over 5 hours.

RESULTS

The mean rabbit rectal temperatures recorded over the test period are shown in Table 2, from which it may be seen that the rise in temperature was less for those rabbits injected with the glycopeptide than for those injected with the known whole cell C.parvum material, at all the dosages tested.

Table 2.

| Rectal Temperature from Pyrogenicity tests in rabbits for whole cell C. parvum and for glycopeptide of the present invention. | | | |
|---|---|---|---|
| | Material injected | Dose mg per rabbit | Mean Temperature rise in ° C |
| A. | Saline | — | 0.1 |
| | C. parvum | 2.8 | 1.55 |
| | whole cells | 0.93 | 1.45 |
| | | 0.31 | 1.2 |
| B. | Saline | — | 0.2 |
| | Glycopeptide | 2.8 | 1.2 |
| | | 0.93 | 1.35 |
| | | 0.31 | 1.0 |

References

1. Prevot, A.-R., & Fredette, V., (1966) 'Manual for the classification and determination of the anaerobic bacteria', Lea and Febiger, Philadelphia, U.S.A.
2. Prevot, A.-R., J. Retic. Soc. 1 115 (1964)
3. Mackie & McCartney's Handbook of Bacteriology p. 233 Edited by R. Cruickshank, 10th Ed., Livingstone, Edinburgh & London, 1960.
4. ibid p. 192
5. ibid p. 234

6. ibid p. 309
7. ibid p. 308
8. Nature 202 (4930) p. 364–366, 25th April 1966.
9. Adlam C. & M. T. Scott, J. Med. Microbiol. 6 261 (1973).
10. Data for Biochemical Research Ed. Dawson, R.M.C., Daphne C. Elliott, W. H. Elliott & K. M. Jones, 2nd Edn. O.U.P., Oxford 1969 p. 618.
11. Spiro, R. G. Methods in Enzymology 8 3 (1966) (Ed. Neufeld, E. F. & Ginsberg, V., pub. Academic Press New York & London.
12. Adlam, C., Broughton, E. S. & Scott, M. T., Nature, New Biol. 235, 219 (1972).
13. Nussenzweig, Ruth S. Expl. Parasitol., 21, 224 (1967).
14. Woodruff, M. F. A. & Boak, J. L., Brit. J. Cancer 20 345 (1966).
15. Sartorelli A. C., Fischer D. S. & Downs W. G., J. Immunology 96 676 (1966).
16. Westphal, O. & Jann, K., Methods in Carbohydrate Chemistry 5 83 (1966), Ed. Whistler, pub. Academic Press, New York & London.
17. Adlam C., J. Med Microbiol., 6 527 (1973)

What we claim is:

1. An immunostimulating glycopeptide suitable for use in conferring on mammals or birds a resistance to Sarcoma 180T/G tumour and pathogenic microoganisms which glycopeptide is obtainable from the cell wall of an immunostimulating bacterium belonging to the Actinomycetaceae family of Prevot's classification, which glycopeptide is substantially insoluble in water, physiological saline, methanol, ethanol, phenol, chloroform, dioxan, pyridine, dimethylformamide, diethylene glycol, and hexane; has an absorption in the Infra-red spectrum at 1550 and 1660 cm$^{-1}$ consistent with the presence of peptide; has an absorption in the Infra-red spectrum between 950 and 1100 cm$^{-1}$ with a maximum absorption at 1050 to 1070 cm$^{-1}$ consistent with the presence of carbohydrate; has little or no lipid absorption in the Infra-red spectrum at 2850 to 2950 cm$^{-1}$; and which glycopeptide, after intravenous administration, increases the liver and spleen weight of mice, and increases the life expectancy of mice with tumours, 2. A glycopeptide as claimed in claim 1 wherein the immunostimulating bacterium is a member of the Corynebacterium genus.

3. A glycopeptide as claimed in claim 2 wherein the immunostimulating bacterium is a member of the Corynebacterium parvum species.

4. A process for obtaining a glycopeptide as defined in claim 1 comprising the steps of culturing the immunostimulating Actinomycetaceae bacterial cells; recovering cultured bacterial cells from the culture; and subjecting the cultured bacterial cells to biphasic solvent extraction using one phase comprising water and a second phase comprising an aryl alcohol to as to yield the glycopeptide as insoluable residue.

5. A process as claimed in claim 4 wherein the cultured bacterial cells are subjected to lysis prior to biphasic solvent extraction.

6. A process as claimed in claim 4 wherein the biphasic solvent extraction comprises the steps of contacting the bacterial cells and/or a lysate thereof with the water and the aryl alcohol followed by centrifugation of the resulting mixture, removal of the aqueous phase and removal of the alcoholic phase to yield a sediment containing an upper layer comprising a white finely divided suspension which is collected to yield the glycopeptide.

7. A process as claimed in claim 6 wherein the aryl alcohol is unsubstituted phenol.

8. A glycopeptide as claimed in claim 1 wherein the immunostimulating bacterium belongs to the strain of the Corynebacterium parvum species having the Wellcome Culture Collection No. CN 6134.

9. A process as claimed in claim 4 wherein the immunostimulating bacterial cells are of the Corynebacterium genus.

10. A process as claimed in claim 9 wherein the immunostimulating bacterial cells are of the Corynebacterium parvum species.

11. A process as claimed in claim 4 wherein the immunostimulating bacterial cells are of the strain of the Corynebacterium parvum species having the Wellcome Culture Collection No. CN 6134.

* * * * *